(12) United States Patent
Smith et al.

(10) Patent No.: US 11,413,083 B2
(45) Date of Patent: Aug. 16, 2022

(54) SPRING LOADED MICROFRACTURE IMPACTOR

(71) Applicant: Zimmer, Inc., Warsaw, IN (US)

(72) Inventors: Joseph Smith, Bluffton, IN (US); Christopher Bragan, North Webster, IN (US)

(73) Assignee: Zimmer, Inc., Warsaw, IN (US)

( * ) Notice: Subject to any disclaimer, the term of this patent is extended or adjusted under 35 U.S.C. 154(b) by 156 days.

(21) Appl. No.: 17/016,318

(22) Filed: Sep. 9, 2020

(65) Prior Publication Data

US 2021/0077171 A1 Mar. 18, 2021

Related U.S. Application Data

(60) Provisional application No. 62/900,883, filed on Sep. 16, 2019.

(51) Int. Cl.
*A61B 17/92* (2006.01)
*A61B 17/84* (2006.01)

(52) U.S. Cl.
CPC ............ *A61B 17/92* (2013.01); *A61B 17/846* (2013.01); *A61B 2017/928* (2013.01)

(58) Field of Classification Search
CPC ................ A61B 17/1604; A61B 17/92; A61B 2017/922; A61B 2017/928
See application file for complete search history.

(56) References Cited

U.S. PATENT DOCUMENTS

2010/0076440 A1* 3/2010 Pamichev .......... A61B 17/1631
606/86 R

FOREIGN PATENT DOCUMENTS

CN    108186107    *    6/2018
CN    108186107 A   *    6/2018  ............. A61B 17/88

* cited by examiner

*Primary Examiner* — Larry E Waggle, Jr.
(74) *Attorney, Agent, or Firm* — Schwegman Lundberg & Woessner, P.A.

(57) ABSTRACT

A microfracture impactor tool including a housing defining a central axis, the housing can include a proximal portion and an opposite distal portion. A handle can be connected to the distal portion of the housing and can extend outward therefrom. The impactor tool can include a grip that is pivotably connected to the proximal portion of the body near the handle. The impactor tool can include an impactor wire configured to impact bone, and a guide tube connected to the distal portion of the housing that is configured to retain the impactor wire.

20 Claims, 8 Drawing Sheets

SPRING LOADED MICROFRACTURE IMPACTOR

CLAIM OF PRIORITY

This application claims the benefit of U.S. Provisional Patent Application Ser. No. 62/900,883, filed on Sep. 16, 2019, the benefit of priority of which is claimed hereby, and which is incorporated by reference herein in its entirety.

BACKGROUND

Articular surfaces of a joint can wear down over time and result in bone to bone contact, which creates a significant amount of pain and discomfort. One solution to this problem is microfracture surgery. In microfracture surgery, damaged cartilage can be scraped away and holes (microfractures) can be created in bone which promotes bleeding from the bone marrow, scabbing, and eventually the growth of new articular cartilage.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The following description and the drawings sufficiently illustrate specific examples to enable those skilled in the art to practice them. Other examples may incorporate structural, process, or other changes. Portions and features of some examples may be included in, or substituted for, those of other examples. Examples set forth in the claims encompass all available equivalents of those claims.

Various devices and techniques for microfracture surgery exist. Current options include hand-held picks, awls, and/or drills. Picks and awls, impacted with a hammer, are often unstable, and prone to skiving. Picks and awls can also create relatively large holes, typically 3 millimeters (mm) or greater, that can slow down the healing process. Picks and awls can become more difficult to use and can become inaccurate when curved or angled. Drills create rotational friction which can cause bone necrosis. Additionally, drill bits are often not flexible enough to reach areas where a curved or angled tool is required, such as hip or shoulder joints. Therefore, it is desirable to provide an improved device and technique.

The devices and methods discussed herein are intended to address current disadvantages of the devices and techniques used in microfracture surgery by providing a microfracture impactor capable of creating small, precise microfractures in bone to enable the regrowth of articular cartilage in a reduced amount of healing time. These microfractures can be created using a microfracture impactor that can be repeatedly discharged using spring force, which can increase microfracture precision and accuracy and can help reduce fatigue of a surgeon. In one example, the microfracture impactor can include a guide tube that can be placed against a surface, such as bone and a grip can be pivoted to load a compression spring. A trigger can be operated to release the compression spring and drive an impactor wire beyond a distal end of the guide tube to impact the bone and to create a microfracture. The microfracture impactor is also capable of being configured to be curved or angled to access otherwise inaccessible areas.

The above discussion is intended to provide an overview of subject matter of the present patent application. It is not intended to provide an exclusive or exhaustive explanation of the invention. The description below is included to provide further information about the present patent application.

Figure 1:
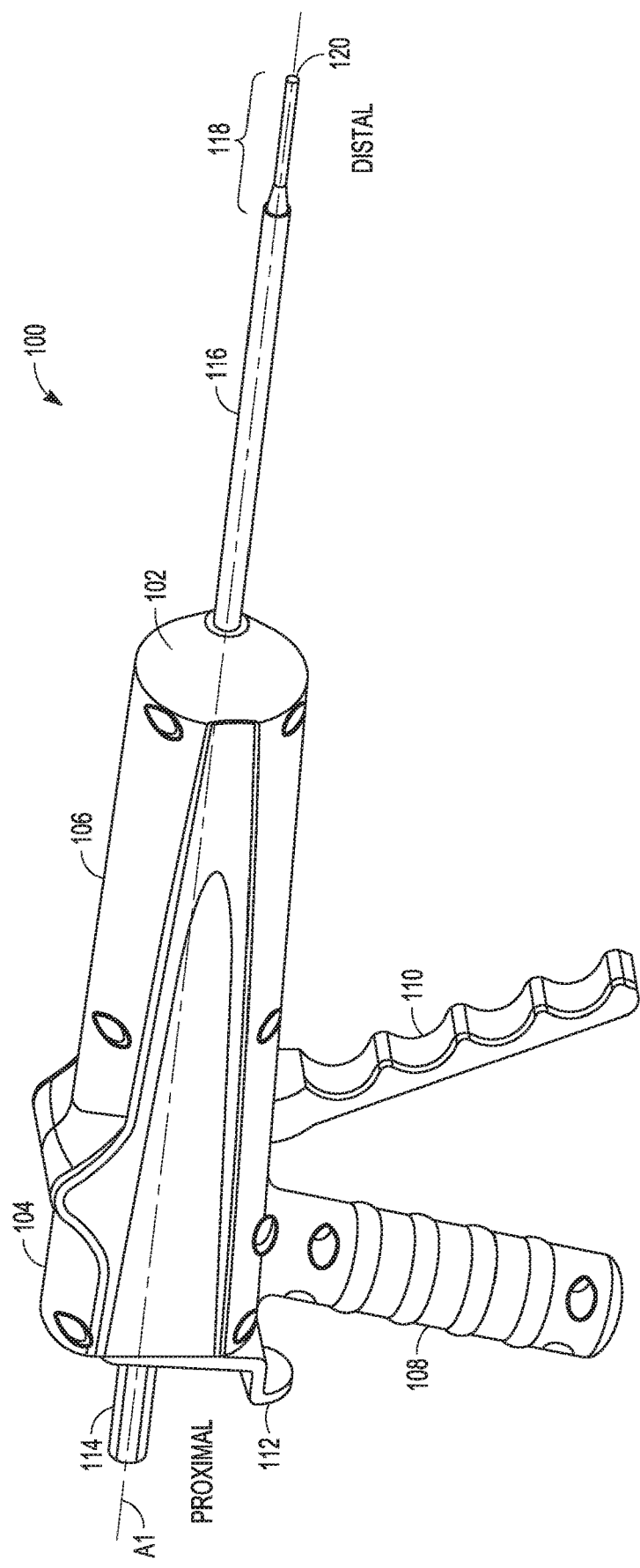
FIG. 1 illustrates an isometric view of a microfracture impactor tool, in accordance with at least one example of the present application.

FIG. 1 illustrates an isometric view of a microfracture impactor tool 100, in accordance with at least one example of the present application. The impactor tool 100 can include a housing 102 (the housing 102 can include a proximal portion 104 and a distal portion 106), a handle 108, a grip 110, a trigger 112, a piston rod 114, a guide tube 116 (the guide tube can include a guide tube tip 118), and an impactor wire 120. Also shown in FIG. 1 are a central axis A1, and orientation indicators Proximal and Distal.

The housing 102 can define the central axis A1. The housing 102 can include a proximal portion 104 and an opposite distal portion 106. The grip 110 can be pivotably connected to the housing 102 using a pin, screw, rivet, or the like. The trigger 112 can be pivotably connected to the proximal portion 104 of the housing 102. The piston rod 114 can be a rigid member located at least partially within the housing 102 and extending lengthwise within the housing 102 along the central axis A1. The piston rod 114 can extend through a proximal end of the housing 102. The piston rod 114 can be configured to moveable within the housing 102 along the central axis A1. The guide tube 116 can be a hollow tube having a substantially cylindrical shape that includes the tip 118. The guide tube 116 can be connected to a distal end of the housing 102. The guide tube 116 can be configured to contain the impactor wire 120.

In the operation of some examples, during a microfracture procedure, an opening in a patient can be created to expose a damaged joint and a corresponding bone or bones, such as a head of a femur. After the joint or bone is exposed, the damaged cartilage can be scraped away in preparation for the creation of micro-fractures. After the bone or bones are prepared for impact, the grip 110 can be pivoted in a proximal direction to load a compression spring (discussed below) located within the housing 102. The tip 118 of the guide tube 116 can be placed against a surface, such as bone, and the trigger 112 can be operated to release the compression spring and drive the impactor wire 120 contained within the guide tube 116 beyond a distal end of the guide tube tip 118 to impact the bone and to create a microfracture in the bone. This impactor process can be repeated to create a plurality of small, precise microfractures in bone. The micro-fractures enable the regrowth of new articular cartilage to replace the damaged cartilage.

Figure 2:
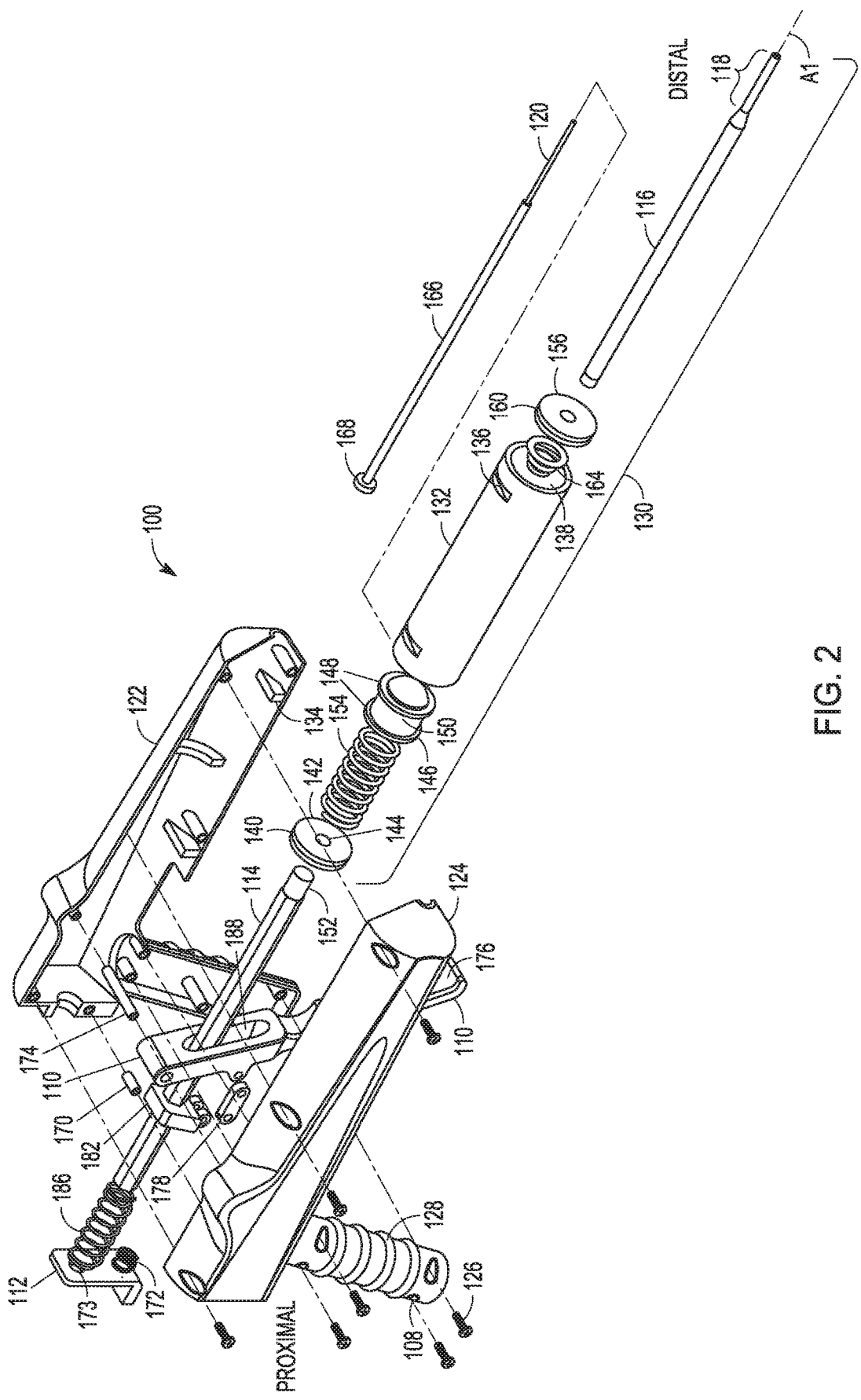
FIG. 2 illustrates an exploded isometric view of an impactor tool and an impactor assembly.

FIG. 2 illustrates an exploded isometric view of the impactor tool 100 and the impactor assembly 130, in accordance with at least one example of the present application. The impactor tool 100 can include the housing 102, the proximal portion 104, the distal portion 106, the handle 108, the grip 110, the trigger 112, the piston rod 114, the guide tube 116, the guide tube tip 118, the impactor wire 120, a left-side housing 122, a right-side housing 124, fasteners 126, gripping features 128, a impactor assembly 130, a piston tube 132, piston tube mounts 134, piston tube recesses 136, tube threads 138, a first tube cap 140, threads 142, an opening 144, a piston 146, an impact region 147, piston-tube contact ridges 148, piston threads 150, piston rod threads 152, a compression spring 154, a second tube cap 156, threads 158, a threaded opening 160, a guide tube threads 162, a return spring 164, a wire holder 166, a wire base 168, a trigger pin 170, a trigger release spring 172, a trigger bore 173, a grip pin 174, finger grooves 176, a linkage 178, a friction plate 182, a grip spring 186, and a grip pocket 188.

The housing 102 can define the central axis A1. The proximal portion 104 and the opposite distal portion 106 can be proximal and distal portions of the housing 102, respectively. The housing 102 can be formed by connecting the left-side housing 122 and the right-side housing 124. The left-side housing 122 and right-side housing 124 can be molded from, but not limited to, plastic, for example, ABS plastic. The left-side housing 122 and right-side housing 124 can be connected using fasteners 126. The fasteners can be made from various metals, for example, but not limited to, stainless steel. The fasteners 126 can be, for example, screws, bolts, or rivets. Other types of fasteners are within the scope of the invention.

The handle 108 of the impactor tool can be molded integrally with the left-side housing 122 and right-side housing 124. The handle 108 can also be molded separately and subsequently connected to the housing 102. The handle 108 can be connected to the proximal portion 104 of the housing 102. The handle 108 can include one or more gripping features 128. The gripping features 128 can be molded with the handle 108 in the form of raised protrusions, bumps, or textured patterns. The gripping features 128 can also be connected to the handle 108 using, for example, fasteners or adhesives after molding.

The impactor assembly 130 of the impactor tool can be positioned within the housing 102 and aligned with the central axis A1. The impactor assembly 130 can include the piston tube 132. The piston tube 132 can be hollow and can be generally cylindrical in shape. The piston tube 132 can be positioned within the housing 102 coaxial with the central axis A1. The piston tube 132 can be made from various metals, for example, but not limited to, stainless steel. The piston tube 132 can include one or more tube recesses 134. The tube recesses 134 can be configured to engage with one or more piston tube mounts 136. The piston tube mounts 136 can be formed on, or molded into, the left-side housing 122 and the right-side housing 124. The piston tube mounts 136 can be inserted into the tube recesses 134 to hold the piston tube 132 in a fixed position within the housing 102 and with respect to the housing 102.

The piston rod 114 can extend within the housing 102 along the central axis A1. The housing 102 can be configured to support the piston rod 114. The piston rod 114 can be configured to be movable within the housing 102 along the central axis A1. The piston rod 114 can be made from various metals, for example, but not limited to, stainless steel.

The impactor assembly 130 can include the first tube cap 140. The first tube cap 140 can include the opening 144 that can be configured to allow the piston rod 114 to extend through the first tube cap 140 into the piston tube 132. The opening 144 can be configured to support and position the piston rod 114 within the impactor assembly 130. The opening 144 can also function as a bearing surface for the piston rod 114 during axial movement of the piston rod 114. The first tube cap 140 can be made from various metals, for example, but not limited to, stainless steel.

The impactor assembly 130 can also include the piston 146, which can be positioned within and supported by the piston tube 132. The piston 146 can be configured to be axially movable within the piston tube 132 along the central axis A1. The impactor assembly 130 can further include the compression spring 154 that can be positioned over the piston rod 114 and within the piston tube 132. The compression spring 154 can be positioned between the piston 146 and the first tube cap 140. The compression spring 154 can be made from various metals, for example, but not limited to, stainless steel or spring steel. The compression spring 154 can be a coil compression spring but can be other types of biasing elements such as a wave spring, gas spring, or the like.

The impactor assembly 130 can further include the second tube cap 156. The second tube cap 156 can include the threaded opening 160, which can be a bore extending through the second tube cap 156 that includes female threading. The guide tube 116 can include the guide tube threads 162 that can be positioned at a proximal end of the guide tube 116. The threaded opening 160 can be configured to engage with the guide tube threads 162 to connect the second tube cap 156 to the guide tube 116. The second tube cap 156 can be made from various metals, for example, but not limited to, stainless steel.

The impactor assembly 130 can also include the return spring 164. The return spring 164 can be positioned within the piston tube 132 and can be positioned between the piston 146 and the second tube cap 156 within the piston tube 132. The return spring 164 can contact, or be connected to, the second tube cap 156. The return spring 164 can be made from various metals, for example, but not limited to, stainless steel. The return spring 164 can be a coil compression spring but can be other types of biasing elements such as a wave spring, gas spring, or the like. The guide tube 116 can be configured to contain and allow the wire holder 166 and the impactor wire 120 to move axially within the guide tube 116. The wire base 168 can be connected to a proximal end of the wire holder 166. The wire base 168 can be positioned within the piston tube 132 between the piston 146 and the return spring 164. The wire base 168 can be configured to be impacted by the piston 146.

The wire holder 166 can be configured to extend axially within the guide tube 116 through the threaded opening 160 in the second tube cap 156 and into the piston tube 132. The wire holder 166 can extend axially within the piston tube 132 between the wire base 168 and the second tube cap 156. The wire holder 166 and impactor wire 120 can extend axially within the return spring 164 located between the wire base 168 and the second tube cap 156.

The impactor wire 120 can extend axially within the guide tube 116. The impactor wire 120 can be connected to a distal end of the wire holder 166. The impactor wire 120 and the wire holder 166 can be configured to be axially movable within the guide tube 116. The wire holder 166 can extend around, or laterally encompass, a length of the impactor wire 120 to strengthen and guide the axial movement of the impactor wire 120 within the guide tube 116. The impactor wire 120 can extend beyond the tip 118, or a distal end, of the guide tube 116. In one example, the impactor wire 120 can extend beyond the tip 118 of the guide tube 116 by about 8 mm. In other examples, the impactor wire 120 can extend beyond the tip 118 of the guide tube 116 by 4 mm, 5 mm, 6 mm, 7 mm, 8 mm, 9 mm, 10 mm, or the like. The extension of the impactor wire 120 beyond the tip 118 can be limited by the wire base 168. The wire base 168 can move axially, in a distal direction, within the piston tube 132 when impacted by the piston 146. The second tube end 156 can be configured to engage the wire base 168 to limit the distal movement of the wire base 168 and the impactor wire 120.

In one example, the impactor wire 120 can measure about 1 mm in diameter. In other examples, the impactor wire 120 can measure 0.75, 0.80, 0.90, 1.10, 1.25, 1.5 mm in diameter, or the like. The relatively small diameter of the impactor wire 120 can create microfractures that help reduce the chance of bone necrosis and can help reduce the healing time, as the impactor wire 120 generates less heat and trauma when impacting and penetrating bone than other methods. The impactor wire 120, the wire holder 166, and the base 168 can be made from various metals and alloys including, but not limited to, nickel titanium alloys. The wire holder 166 can also be made from stainless steel to provide additional strength. The guide tube 116 can be made from various metals including, but not limited to, stainless steel. The guide tube 116 can be configured to be laterally rigid and strengthen the impactor wire 120 and wire holder 166.

The impactor tool 100 can include a trigger 112 that is pivotably connected to the proximal portion 104 of the housing 102. The trigger 112 can be connected to the housing 102 with the trigger pin 170. The trigger 112 can be made from various metals, for example, but not limited to, stainless steel. The trigger release spring 172 can be positioned between the trigger 112 and a proximal end of the housing 102 to bias the trigger in a proximal direction relative to the housing 102. The trigger release spring 172 can be made from various metals, for example, but not limited to, stainless steel. The trigger release spring can be a coil compression spring but can be other types of biasing elements such as a wave spring, gas spring, or the like. The trigger 112 can be configured to be engageable with the piston rod 114. The trigger 112 can include a trigger bore 173 configured to receive the piston rod 114 therethrough. The piston rod 114 can move through and engage with the trigger bore 173.

The impactor tool 100 can include the grip 110 that can be pivotably connected to the proximal portion 104 of the housing 102. The grip 110 can be made from various metals, for example, but not limited to, stainless steel. The grip 110 can be connected to the left side housing 122 and the right-side housing 124 with the grip pin 174. The grip 110 can include the finger grooves 176 formed in a distal surface of the grip 110. The finger grooves 176 can provide additional grip when using the grip 110. The grip 110 can be connected to the linkage 178 with the grip-linkage pin 180. The linkage 178 can connect the grip 110 to the friction plate 182 where the friction plate-linkage pin 184 can secure the connection. The friction plate 182 can be configured to be engageable with the piston rod 114. The grip pin 174, grip-linkage pin 180, and friction plate-linkage pin 184 can be made from various metals, for example, but not limited to, stainless steel.

The grip spring 186 can be positioned within the housing 102 and over the piston rod 114 between a proximal end of the housing 102 and the friction plate 182. The grip 110 can be biased in a distal position relative to the housing 102 by the grip spring 186. When the grip 110 is in a distally biased position, the friction plate 182 can be disengaged from the piston rod 114. The friction plate 182 can be configured to move axially within the housing 102 along the central axis A1. The grip spring 186 can be made from various metals, for example, but not limited to, stainless steel. The grip spring 186 can be a coil compression spring but can be other types of biasing elements such as a wave spring, gas spring, or the like.

The friction plate 182 can engage the piston rod 114 when the friction plate 182 is moved in a proximal direction. The friction plate 182 can be configured to be disengaged from the piston rod 114 when the friction plate 182 is moved in a distal direction. When the grip 100 is pivoted in a proximal direction, the friction plate 182 can engage with the piston rod 114 and transfer the proximal movement of the grip to the piston rod 114, moving the piston rod 114 and therefore the piston 146 proximally, compressing the compression spring 154. The grip spring 186 can return the grip 110 to a distally biased position after the grip 110 is released. The grip 110 can include a grip pocket 188. The grip pocket 188 can be an opening in the grip 110 that can allow the piston rod 114 to extend through the grip 110. The grip pocket 188 can be configured to be un-engageable with the piston rod 114 when the grip 110 is released and moved in a distal direction by the grip spring 186. Further details of operation of the impactor 100 are discussed below with respect to FIGS. 4A-4C.

Figure 3:
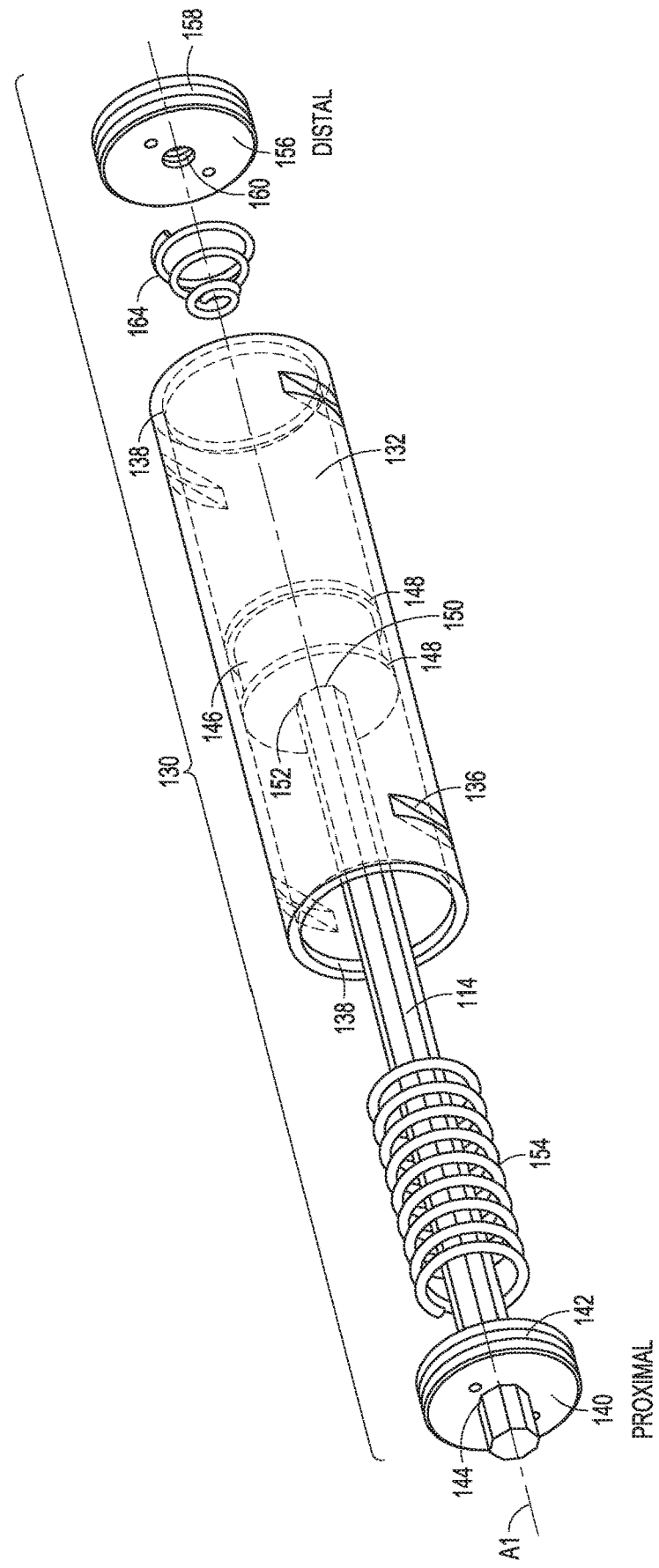
FIG. 3 illustrates an isometric view of a portion of an impactor assembly, in accordance with at least one example of the present application.

FIG. 3 illustrates an isometric view of a portion of the impactor assembly 130, in accordance with at least one example of the present application. The impactor assembly 130 of FIG. 3 can be consistent with the assembly discussed above with respect to FIGS. 1 and 2; further details of the impactor assembly are discussed with respect to FIG. 3.

The piston tube 132 can include the tube threads 138. The tube threads 138 can be formed in a proximal end and in a distal end of the piston tube 132. The first tube cap 140 can include the threads 142, which can be configured to engage with the tube threads 138 that can be positioned at a proximal end of the piston tube 132 to connect the first tube cap 140 to the piston tube 132. The second tube cap 156 can include the threads 158. The piston 146 can be generally cylindrical in shape. The piston 146 can also have an impact region 147 that can be generally cone shaped. The piston 146 can be machined from, for example, but not limited to, stainless steel. The piston 146 can include the piston-tube contact ridges 148. The piston-tube contact ridges 148 can extend radially from a body of the piston 146. The piston tube contact ridges 148 can be machined or otherwise formed on piston 146.

The piston-tube contact ridges 148 can be configured to contact an inner surface of the piston tube 130 to assist in guiding axial movement of the piston 146 within the piston tube 132. The piston-tube contact ridges 148 can help to decrease friction between the piston 146 and the piston tube 132 as the piston-tube contact ridges 148 can reduce the surface area of the piston 146 that contacts the piston tube 132.

In an example, a total axial travel of the piston 146 within the piston tube 132 can be 1.5 inches. In other examples, the axial travel of the piston can be 1, 1.25, 1.75, 2 inches, or the like. In some examples, piston travel can be adjustable, such as through compression spring replacement or through other adjustments to components of the impactor assembly 130. The piston 146 can include the piston threads 150. The piston threads 150 can be formed in a proximal end of the piston 146. The piston rod 114 can also include the piston rod threads 152. The piston rod threads 152 can be formed in a distal end of the piston rod 114. The piston threads 150 can be configured to be engageable with the piston rod threads 152 to couple the piston 146 to the piston rod 114.

Figure 4A:
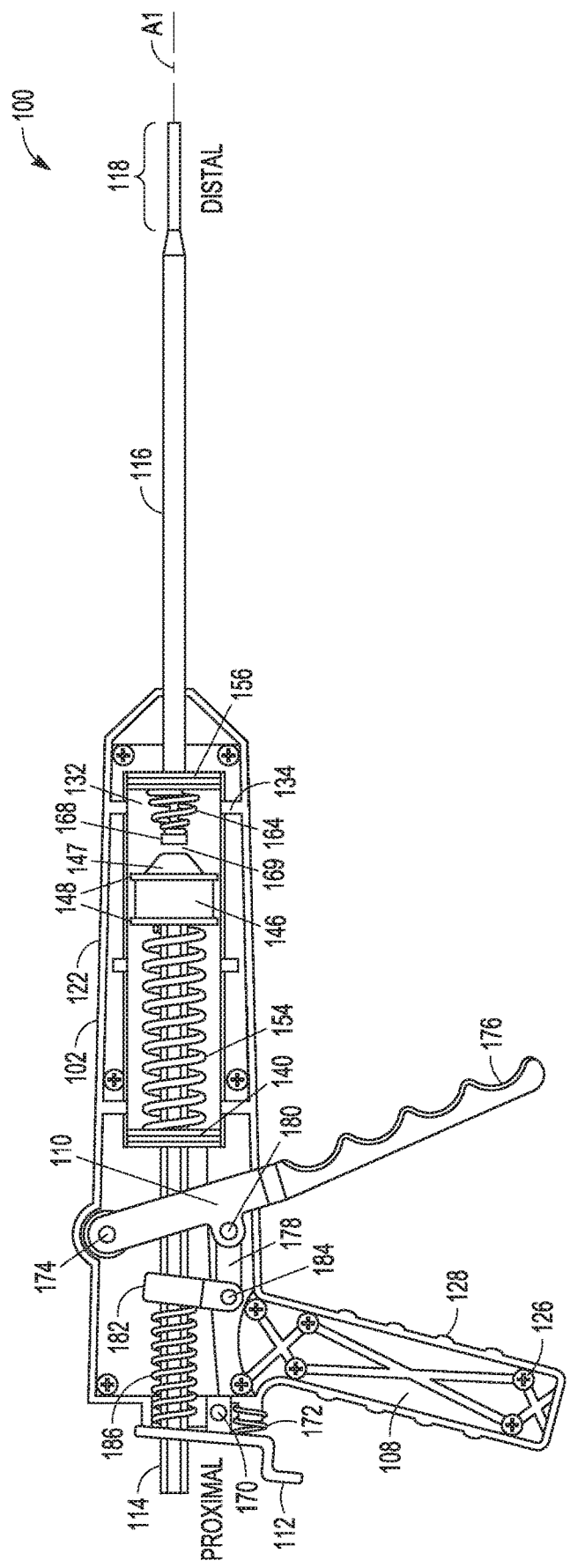
FIG. 4A illustrates a side isometric view of an impactor tool and an impactor assembly in a first condition, in accordance with at least one example of the present application.
Figure 4B:
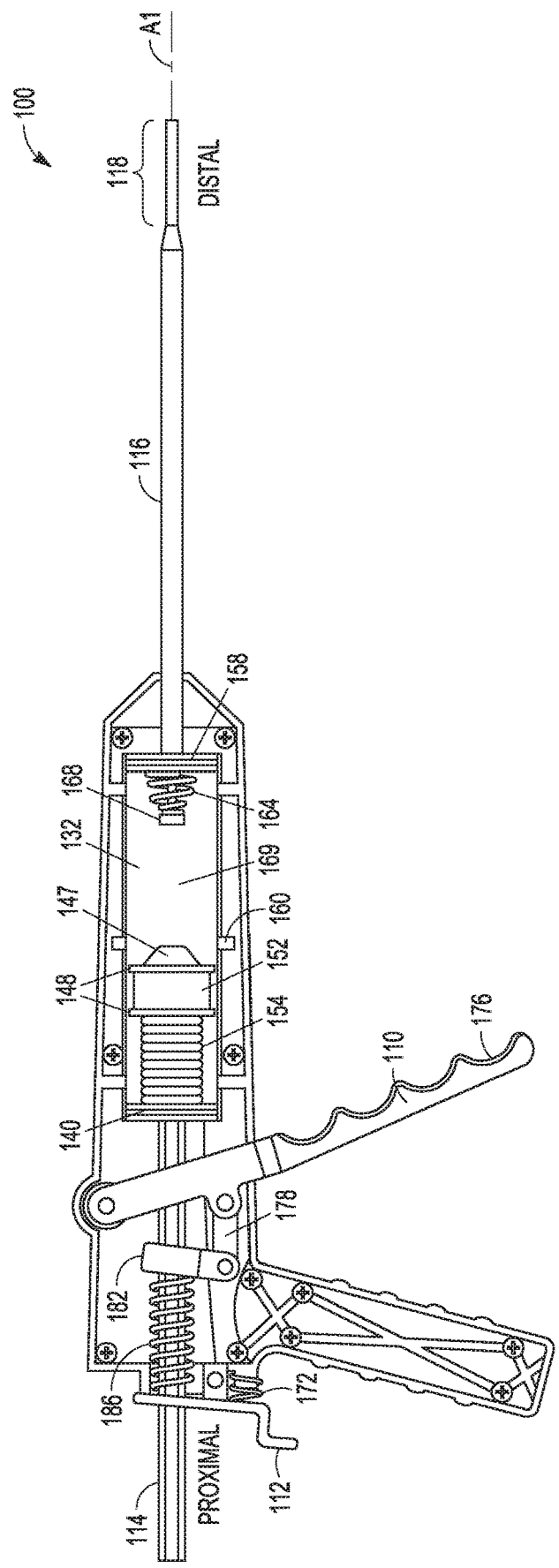
FIG. 4B illustrates a side isometric view of an impactor tool and an impactor assembly in a second condition, in accordance with at least one example of the present application.
Figure 4C:
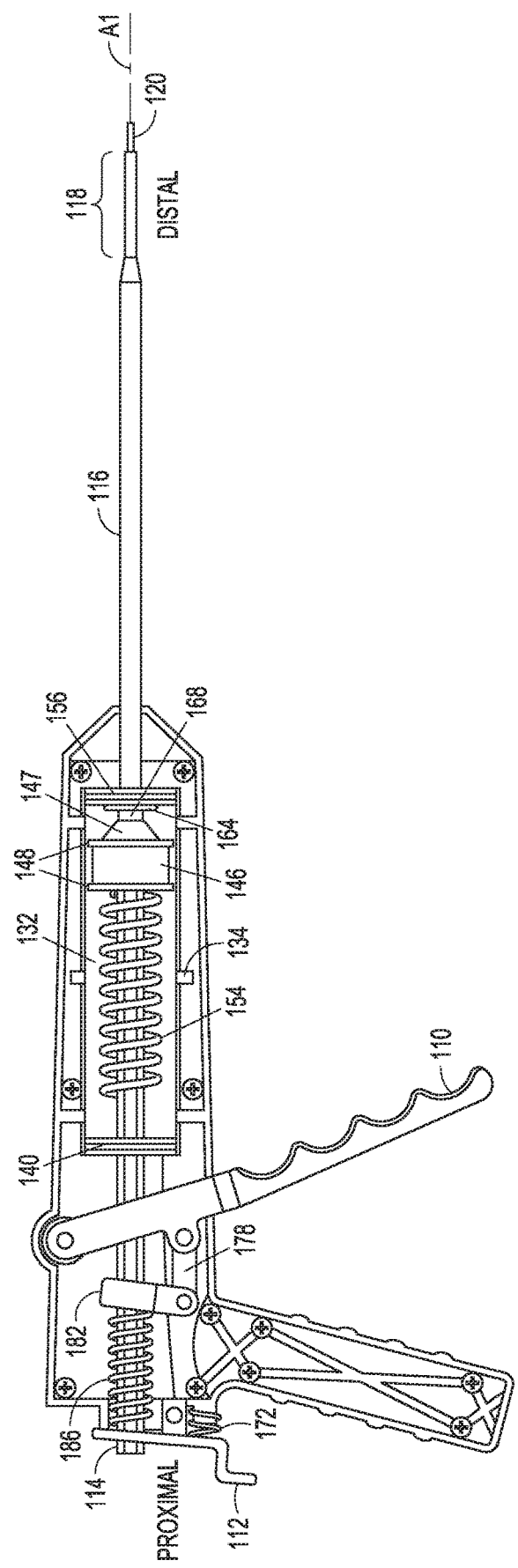
FIG. 4C illustrates a side isometric view of an impactor tool and an impactor assembly in a third condition, in accordance with at least one example of the present application.

FIGS. 4A-4C illustrate side isometric views of the impactor tool 100 and the impactor assembly 130 in a first, a second, and a third condition, respectively, in accordance with at least one example of the present application. The microfracture impactor 100 can further include a gap 169, a grip linkage pin 180, and a friction plate linkage pin 184. FIGS. 4A-4C are discussed below concurrently.

FIG. 4A shows that the compression spring 154 can be in a resting, or uncompressed, state. Then, in operation, the grip 110 can be pivoted proximally toward the handle 108. As the grip 110 pivots, the linkage 176 can transfer the proximal movement of the grip 110 to the friction plate 182. The friction plate 182 can be configured to move axially within the housing 102 along the central axis A1. The friction plate 182 can be angled such that it creates sufficient friction on the piston rod 114 when the friction plate 182 is moved in a proximal direction to engage the piston rod 114 and transfer proximal movement of the linkage 176 to the piston rod 114. The proximal movement transferred to the piston rod 114 by the linkage 176 and friction plate 182 can move the piston rod 114 proximally through the trigger bore 173 and load the compression spring 154 by compressing the compression spring 154 between the piston 146 and the first tube cap 140. As the piston 146 and piston rod 114 move proximally, and the first tube cap 140 remains stationary, causing the compression spring 154 to be in a compressed, or loaded, state, as shown in FIG. 4B.

After the grip 110 pivots and is released, the grip spring 186 can engage the friction plate 182 to move the linkage 178 to return the grip 110 to a distally biased position. During this movement, the friction plate 182 can pivot about the friction plate-linkage pin 184 and disengage from the piston rod 114 when moved in a distal direction, allowing the grip 110 to return to a proximally biased position. The trigger bore 173 can hold the piston rod 114 in place when the grip is returned to a proximal position through friction engagement between the trigger bore 173 and the piston rod 114. The grip 110 can be pivoted more than one time to further load the compression spring 154. The force required to pivot the grip 110 can increase after each subsequent pivot of the grip 110.

The ability of the grip 110 to be pivoted more than one time to load the compression spring 154 can provide several benefits to the user when using the impactor 100. A user can operate the impactor 100 one-handed due to force multiplication in the leverage created by the relative lengths and angles of the grip 110, linkage 178, and friction plate 182. Additionally, the grip 110 can provide an option to slowly load the compression spring 154 over several cycles of the grip 110 to ensure that the compression spring 154 will have sufficient stored energy to drive the impactor wire 120 into bone while reducing the force that must be exerted on the grip 110 in a single motion. Additionally, this feature can allow the user to selectively choose how much force the compression 154 will deliver to the impactor wire 120. It may be desirable to use less force, for example, if the depth of impactor wire 120 penetration needs to be reduced.

When the trigger 112 is forced in a distal direction, the trigger 112 can pivot and disengage the piston rod 114 from the trigger bore 173. When the piston rod 114 is released from the trigger 112, the energy stored in the loaded compression spring 154 can force the piston rod 114 and the piston 146 to move axially and rapidly in a distal direction within the piston tube 132. The piston 146 can then impact the wire base 168 of the impactor wire 120 to force the wire to extend beyond a tip of the guide (where the wire can impact bone to create a microfracture), as shown in FIG. 4C. The momentum of the moving piston 146 can force the compression spring 154 to overextend, beyond its resting length, and impact the wire base 168. When the trigger 112 is released, the trigger release spring 172 can return the trigger 112 to a proximally biased position and the trigger 112 can re-engage with the piston rod 114.

FIG. 4C shows an example of the compression spring 154 in an overextended state. When the compression spring 154 is in a relaxed state (not compressed), the piston 146 and the wire base 168 can be separated by the gap 169. The gap 169 can be a free space between a distal end of the piston 146 and a proximal end of the wire holder 168. In some examples, the compression spring 154 can be selected such that it must overextend to cause the piston 146 to travel the gap 169. The gap 169 can be positioned between the piston 146 and the wire base 168 can ensure that the return spring 164 can return the wire base 168 to its resting position after the wire base 168 is impacted by the piston 146; without interference from the compression spring 154 or the piston 146. In one example, the gap 169 can measure about 0.25 inches. In other examples, the gap 169 can measure 0.10-0.5 inches.

The wire base 168 can be configured to receive the impact of the piston 146. When the piston 146 impacts the wire base 168, the piston 146 can drive the impactor wire 120 in distal direction, which can cause a distal end of the impactor wire 120 to extend beyond the tip 118 of the guide tube 116. The impactor wire 120 can be configured to extend from the tip 118 of guide tube 116 into bone. The extension of the impactor wire 120 beyond the tip 118 of the guide tube 116, or the corresponding penetration of the impactor wire 120 into bone, can be limited by the second tube cap 156 (and by the return spring 158). When the piston 146 impacts the wire base 168, the piston 146 can drive the wire base 168 in a distal direction until the wire base 168 contacts the second tube cap 156. The second tube cap 156 together with the return spring 158 can stop the distal movement of the piston 146 and piston rod 114.

The return spring 158 can be positioned between the wire base 168 of the wire holder 164 and the second tube cap 154. When the wire base 168 is impacted, the distal movement of the base 168 can load the return spring 158 by compressing it against the stationary second tube cap 156. After the impactor wire 120 extends beyond the tip 118 of the guide tube 116 and the compression spring 154 is unloaded, the return spring 158 can unload and force the wire base 168 to move back in a proximal direction. The proximal movement of the wire base 168 can force the impactor wire 120, wire base 168, and wire holder 166 to move back in a proximal direction and withdraw the distal end of the impactor wire 120 out of the bone and into the guide tube 116. The guide tube 116, impactor wire 120, wire holder 166, and wire base 168 can be replaced between uses for sterilization purposes. The threaded engagement between the second tube cap 156 and piston tube 132 can allow the guide tube 116, the impactor wire 120, and the wire holder 166 to be replaced without de-coupling the left-side housing 122 from right-side housing 124. The other components of the impactor tool 100, including the housing 102, can be sterilized, for example, but not limited to, autoclaving.

Figure 5A:
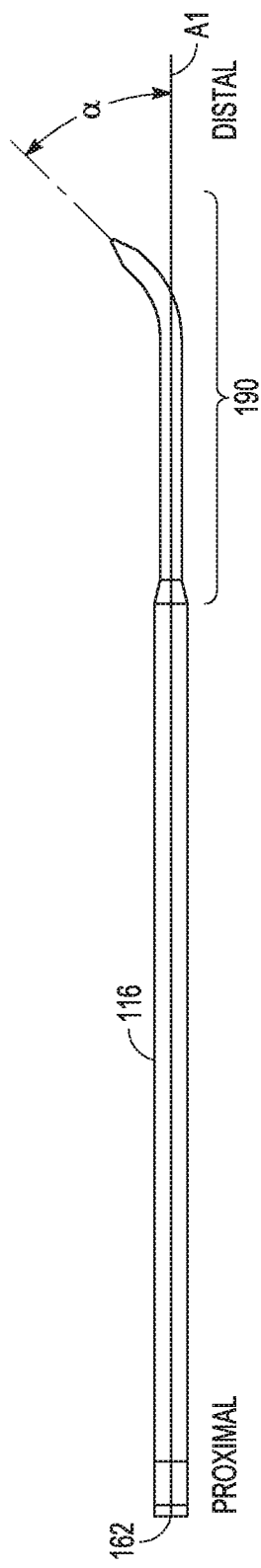
FIG. 5A illustrates a side view of a guide tube, in accordance with at least one example of the present application.
Figure 5B:
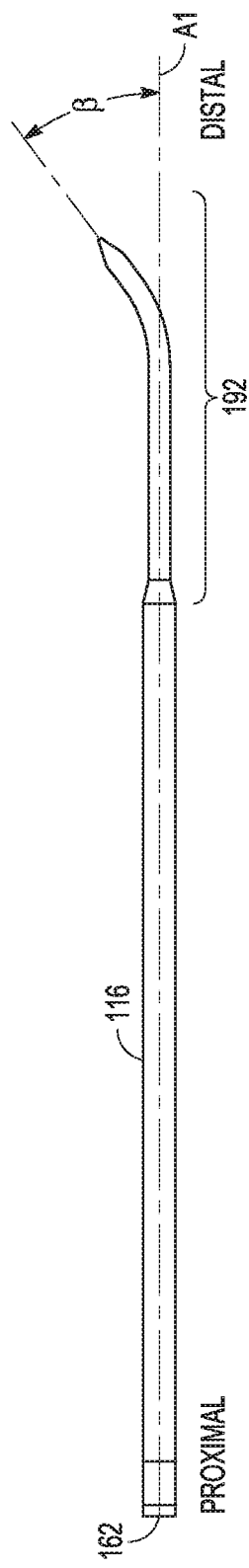
FIG. 5B illustrates a side view of a guide tube, in accordance with at least one example of the present application.
Figure 5C:
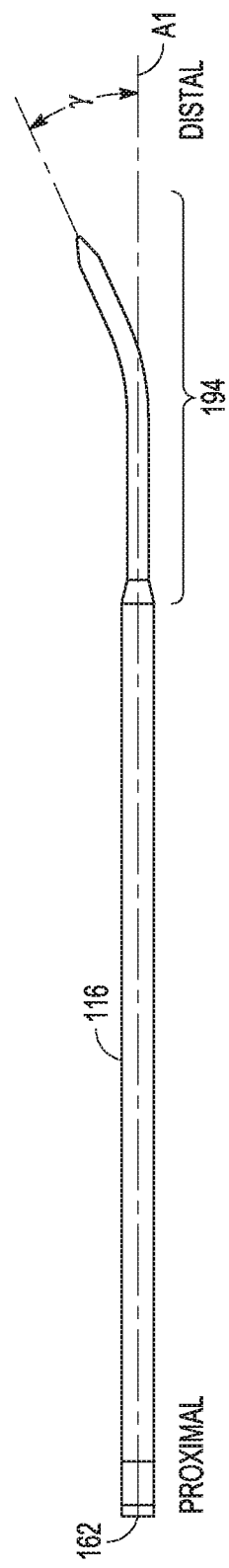
FIG. 5C illustrates a side view of a guide tube, in accordance with at least one example of the present application.

FIGS. 5A-5C illustrate side views of a guide tube, in accordance with at least some examples of the present application. FIGS. 5A-5C are discussed below concurrently. In the example of FIG. 5A, the guide tube 116A can have a guide tube tip 190 that curves at an angle α relative to the central axis A1 that is a 60-degree angle. In the example of FIG. 5B, the guide tube 116 can have a guide tube tip 192 that curves at an angle β relative to the central axis A1 that is a 45-degree angle. In the example of FIG. 5C, the guide tube 116 can have a guide tube tip 194 that curves at an angle γ relative to the central axis A1 that is a 30-degree angle. Other curvature angles are within the scope of the invention.

The angled guide tube tips 190, 192, and 194 can be used to reach otherwise difficult-to-reach places, such as hip joints, or other areas that certain devices, such as drills, are unable to reach. The impactor wire 120 and wire holder 166 can be made from flexible metals or composites, such as, but not limited to nickel-titanium alloys (e.g., Nitinol). Nickel-titanium is one example of a material that is suitably flexible and allows the impactor wire 120 and wire holder 166 to bend sufficiently for use with angled guide tube tips 190, 192, and 194, but that is rigid enough to create a microfracture in a bone even when bent at the angles described. Though FIGS. 5A-5C discuss guide tubes at angles between 30 and 60 degrees, guide tubes having great or larger angles can be used, such as 5, 10, 15, 20, 25, 40, 50, 55, 65, 70, 75, 80, 90 degrees, or the like.

Figure 6:
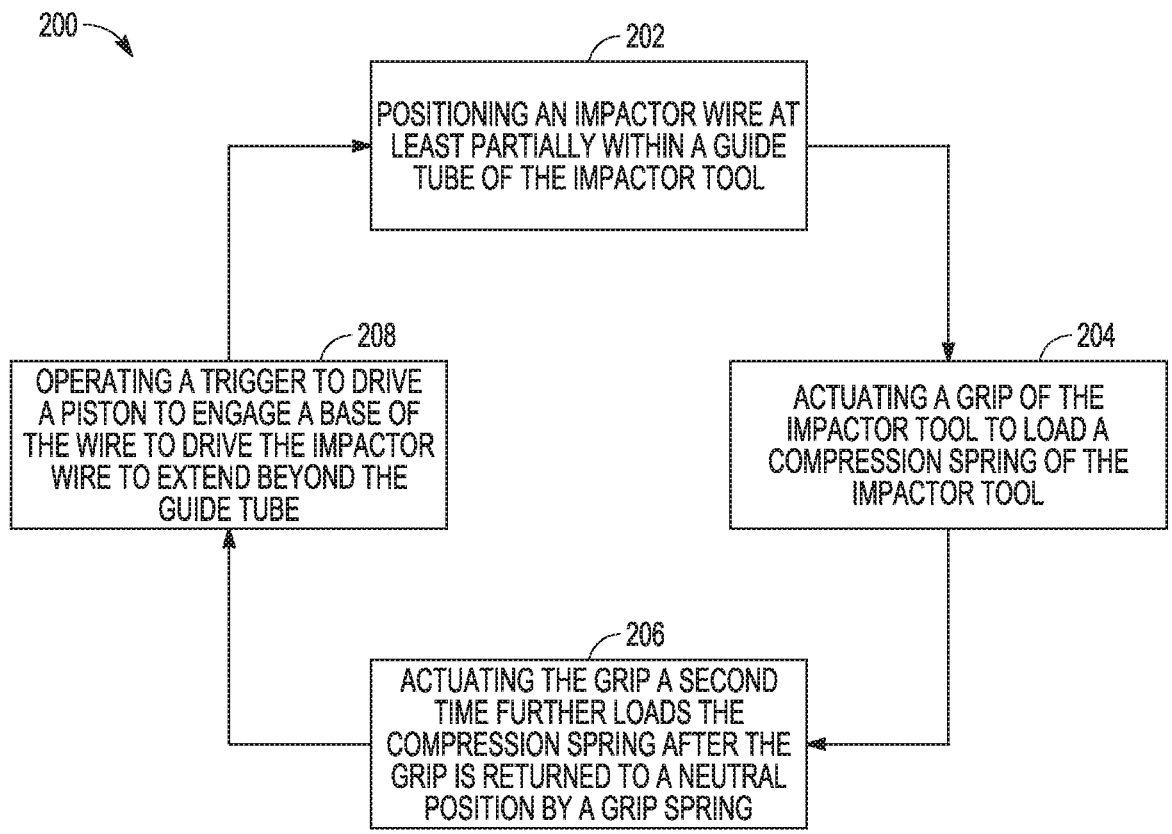
FIG. 6 illustrates an example of a method for using an impactor tool, in accordance with at least one example of the present application.

FIG. 6 illustrates an example of a method 200 for using an impactor tool, in accordance with at least one example of the present application. The steps or operations of the method 200 are illustrated in a particular order for convenience and clarity; many of the discussed operations can be performed in a different sequence or in parallel without materially impacting other operations. The method 200 as discussed includes operations that can be performed by multiple different actors, devices, and/or systems. It is understood that subsets of the operations discussed in the method 200 can be attributable to a single actor, device, or system could be considered a separate standalone process or method.

In one or more examples, a first step can be positioning an impactor wire at least partially within a guide tube of the impactor tool. In one or more examples, a second step may be actuating a grip of the impactor tool to load a compression spring of the impactor tool. In one or more examples, an optional third step can be actuating the grip a second time to further load the compression spring after the grip is returned to a neutral position by a grip spring. In one or more examples, a fourth step may be operating a trigger to drive a piston to engage a base of the wire to drive the impactor wire to extend beyond the guide tube.

In one or more examples, a user can position an impactor wire 120 located at least partially within a guide tube 116 of the impactor tool 100 (202). Positioning the guide tube 116 can include inserting the guide tube through a patient's skin or into a cannula. Positioning the guide tube 116 can include resting or bracing the tip of the guide tube 118 on a bone or joint. The user can actuate a grip 110 of the impactor tool 100 to load a compression spring 154 of the impactor tool 100 (204). A user can optionally actuate the grip 110 more than once (206). A user can operate a trigger 112 to drive a piston 154 to engage a base 168 of the impactor wire 120 to drive the impactor wire 120 to extend beyond the tip 118 of the guide tube 116 (208). Steps 202-208 can be repeated more than once to create two or more microfractures.

Notes and Examples

The following, non-limiting examples, detail certain aspects of the present subject matter to solve the challenges and provide the benefits discussed herein, among others.

Example 1 is a microfracture impactor tool comprising: a housing defining a central axis, the housing comprising a proximal portion and an opposite distal portion; a handle connected to the proximal portion of the housing and extending outward therefrom; a grip pivotably connected to the proximal portion of the body near the handle; an impactor wire configured to impact bone; a guide tube connected to the distal portion of the housing and configured to retain the impactor wire; a piston rod supported by the housing and engageable with the grip, the piston rod movable relative to the housing along the central axis; and a piston located within the housing and connected to the piston rod, the piston configured to engage the impactor wire to cause the impactor wire to extend beyond a distal end of the guide tube to impact the bone.

In Example 2, the subject matter of Example 1 optionally includes an impactor wire holder positionable within the guide tube and configured to support the impactor wire within the guide tube.

In Example 3, the subject matter of Example 2 optionally includes wherein the wire holder comprises a base at a proximal end of the wire holder, the piston configured to impact the wire holder base to drive the impactor wire beyond the distal end of the guide tube.

In Example 4, the subject matter of any one or more of Examples 1-3 optionally include wherein one or more of the impactor wire and the wire holder is made from a nickel-titanium alloy.

In Example 5, the subject matter of any one or more of Examples 1-4 optionally include wherein the guide tube is curved relative to the central axis.

In Example 6, the subject matter of any one or more of Examples 1-5 optionally include wherein a proximal end of the guide tube is threaded and is configured to engage a threaded distal end of the housing.

In Example 7, the subject matter of any one or more of Examples 1-6 optionally include a trigger connected to a proximal end of the housing, and a friction plate coupled to the housing, wherein the piston rod passes through and is engageable with the friction plate.

In Example 8, the subject matter of Example 7 optionally includes wherein the grip is operable to move the piston rod distally through the friction plate to cause the piston to engage and compress (or load) a compression spring, the friction plate engageable with the piston rod to hold a position of the piston rod when the grip is returned to a neutral position.

In Example 9, the subject matter of Example 8 optionally includes wherein the trigger is operable to release the friction plate from the piston rod and unload the compression spring.

Example 10 is a microfracture impactor assembly comprising: a housing defining a central axis, the housing comprising a proximal portion and an opposite distal portion; a piston rod supported by the housing, the piston rod movable relative to the housing along the central axis; an impactor assembly positioned within the housing, the impactor assembly including: a piston tube including a first tube cap at a proximal end of the tube, the piston rod extending through the first tube cap, and a second tube cap at a distal end of the tube; a compression spring within the piston tube and connected to the piston and engaging the first tube cap; a piston connected to the piston rod and movable therewith; a wire holder extending through the second tube cap into the guide tube; an impactor wire supported by the wire holder and movable therewith; and a guide tube connected to the distal portion of the housing and configured to support the impactor wire therein; a trigger connected to a proximal end of the housing, the trigger operable to release the piston to impact the impactor wire to drive the impactor wire to extend beyond the guide tube.

In Example 11, the subject matter of Example 10 optionally includes a handle connected to the proximal portion of the housing and extending outward therefrom.

In Example 12, the subject matter of any one or more of Examples 10-11 optionally include a grip pivotably connected to the proximal portion of the body near the handle.

In Example 13, the subject matter of any one or more of Examples 10-12 optionally include a friction plate coupled to the housing, wherein the piston rod passes through and is engageable with the friction plate.

In Example 14, the subject matter of Example 13 optionally includes a linkage connected to the friction plate and the grip, wherein pivoting of the grip moves the friction plate and loads the compression spring.

In Example 15, the subject matter of Example 14 optionally includes wherein the impactor includes a grip spring positioned over the piston rod between the friction plate and proximal end of the housing, the grip spring configured to bias the friction plate and grip distally.

In Example 16, the subject matter of any one or more of Examples 14-15 optionally include wherein the grip is operable to move the piston rod distally through the friction plate to cause the piston to engage and compress (or load) a compression spring, the friction plate engageable with the piston rod to hold a position of the piston rod when the grip is returned to a neutral position.

In Example 17, the subject matter of Example 16 optionally includes wherein the trigger is operable to release the friction plate from the piston rod and unload the compression spring.

In Example 18, the subject matter of any one or more of Examples 10-17 optionally include wherein the impactor assembly includes a wire base, and wherein the compression spring is configured to over-extend beyond its resting length to push the piston into a wire base to drive the impactor wire to extend beyond the guide tube.

In Example 19, the subject matter of any one or more of Examples 10-18 optionally include wherein the impactor includes a trigger release spring between the trigger and the distal end of the housing configured to bias the trigger proximally.

In Example 20, the subject matter of any one or more of Examples 10-19 optionally include wherein the piston rod extends through the proximal end of the housing and through the trigger.

In Example 21, the subject matter of any one or more of Examples 10-20 optionally include wherein the piston includes a body and ridges extending radially from the body, the ridges configured to contact an inner surface of the piston tube.

In Example 22, the subject matter of any one or more of Examples 10-21 optionally include wherein the wherein the impactor assembly includes a return spring between the base of the impactor wire and the second tube cap, the return spring configured to bias the impactor wire proximally.

In Example 23, the subject matter of any one or more of Examples 10-22 optionally include wherein a distal end of the guide tube is threadably securable to the second tube cap.

In Example 24, the subject matter of any one or more of Examples 10-23 optionally include wherein the piston tube is supported by the housing and configured to guide the piston axially.

Example 25 is a method for creating a microfracture in bone comprising: actuating a grip of an impactor to load a compression spring of the impactor; positioning a guide tube of the impactor against a surface of a bone to be fractured, a wire located at least partially within the guide tube of the impactor; and operating a trigger to drive a piston to engage a base of the wire to drive the tip of the wire into the bone.

In Example 26, the subject matter of Example undefined optionally includes wherein the actuating the grip a second time further loads the compression spring after the grip is returned to a neutral position by a grip spring.

In Example 27, the subject matter of any one or more of Examples 25-26 optionally include actuating the grip a second time to load the compression spring after the grip is returned to a neutral position by a grip spring.

In Example 28, the subject matter of any one or more of Examples 25-27 optionally include guiding the wire to impact the bone using a curved guide tube.

Example 29 is a method for using an impactor tool comprising: positioning an impactor wire at least partially within a guide tube of the impactor tool; and actuating a grip of the impactor tool to load a compression spring of the impactor tool; operating a trigger to drive a piston to engage a base of the wire to drive the impactor wire to extend beyond the guide tube.

In Example 30, the subject matter of Example 29 optionally includes wherein operating the trigger releases a friction plate from a piston rod connected to the piston and unloads the compression spring.

In Example 31, the apparatuses or method of any one or any combination of Examples 1-30 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein. In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A microfracture impactor tool comprising:
a housing defining a central axis, the housing comprising a proximal portion and a distal portion; a handle connected to the proximal portion of the housing and extending outward therefrom;
a grip pivotably connected to the proximal portion of the housing near the handle;
an impactor wire configured to impact bone;
a guide tube connected to the distal portion of the housing and configured to retain the impactor wire;
a piston rod supported by the housing and engageable with the grip, the piston rod movable relative to the housing along the central axis; and
a piston located within the housing and connected to the piston rod, the piston configured to engage the impactor wire to cause the impactor wire to extend beyond a distal end of the guide tube to impact the bone.

2. The impactor tool of claim 1, further comprising:
an impactor wire holder positionable within the guide tube and configured to support the impactor wire within the guide tube.

3. The impactor tool of claim 2, wherein the wire holder comprises a base at a proximal end of the wire holder, the piston configured to impact the wire holder base to drive the impactor wire beyond the distal end of the guide tube.

4. The impactor tool of claim 2, wherein the impactor wire is made from a nickel-titanium alloy and the wire holder is made from stainless steel.

5. The impactor tool of claim 1, wherein the guide tube is curved relative to the central axis.

6. The impactor tool of claim 1, wherein a proximal end of the guide tube is threaded and is configured to engage a threaded distal portion of the housing.

7. The impactor tool of claim 1, further comprising a trigger connected to the proximal portion of the housing, and a friction plate coupled to the housing, wherein the piston rod passes through and is engageable with the friction plate.

8. The impactor tool of claim 7, wherein the grip is operable to move the piston rod distally through the friction plate to cause the piston to engage and compress a compression spring, the friction plate engageable with the piston rod to hold a position of the piston rod when the grip is returned to a neutral position.

9. The impactor tool of claim 8, wherein the trigger is operable to release the friction plate from the piston rod and unload the compression spring.

10. A microfracture impactor system comprising:
a housing defining a central axis, the housing comprising a proximal portion and a distal portion;
a piston rod supported by the housing, the piston rod movable relative to the housing along the central axis;
a guide tube connected to the distal portion of the housing and configured to support an impactor wire therein;
an impactor assembly positioned within the housing, the impactor assembly including:
a piston tube including a first tube cap at a proximal end of the tube, the piston rod extending through the first tube cap, and a second tube cap at a distal end of the tube;
a piston connected to the piston rod and movable therewith;
a compression spring within the piston tube and connected to the piston and engaging the first tube cap;
a wire holder extending through the second tube cap into the guide tube; and
an impactor wire supported by the wire holder and movable therewith; and
a trigger connected to a proximal portion of the housing, the trigger operable to release the piston to impact the impactor wire to drive the impactor wire to extend beyond the guide tube.

11. The impactor system of claim 10, further comprising a handle connected to the proximal portion of the housing and extending outward therefrom.

12. The impactor system of claim 11, further comprising a grip pivotably connected to the proximal portion of the housing near the handle.

13. The impactor system of claim 12, further comprising:
a friction plate coupled to the housing, wherein the piston rod passes through and is engageable with the friction plate.

14. The impactor system of claim 13, further comprising:
a linkage connected to the friction plate and the grip, wherein pivoting of the grip moves the friction plate and loads the compression spring.

15. The impactor system of claim 14, further comprising:
a grip spring positioned over the piston rod between the friction plate and a proximal end of the housing, the grip spring configured to bias the friction plate and grip distally.

16. The impactor system of claim 14, wherein the grip is operable to move the piston rod distally through the friction plate to cause the piston to engage and compress the compression spring, the friction plate engageable with the piston rod to hold a position of the piston rod when the grip is returned to a neutral position.

17. The impactor system of claim 16, wherein the trigger is operable to release the friction plate from the piston rod and unload the compression spring.

18. The impactor system of claim 10, wherein the impactor assembly includes a wire base, and wherein the compression spring is configured to extend beyond its resting length to push the piston into a wire base to drive the impactor wire to extend beyond the guide tube.

19. The impactor system of claim 10, further comprising: a trigger release spring between the trigger and a distal end of the housing configured to bias the trigger proximally.

20. The impactor system of claim 10, wherein the piston rod extends through the proximal portion of the housing and through the trigger.

\* \* \* \* \*